US 11,712,211 B2

United States Patent
Köpnick et al.

(10) Patent No.: US 11,712,211 B2
(45) Date of Patent: Aug. 1, 2023

(54) CLEANING AND CHARGING PORTABLE X-RAY DETECTORS

(71) Applicant: KONINKLIJKE PHILIPS N.V., Eindhoven (NL)

(72) Inventors: Johannes Köpnick, Neumunster (DE); Eugen Hermann, Hamburg (DE); Hanns-Ingo Maack, Norderstedt (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 17/640,065

(22) PCT Filed: Jan. 28, 2021

(86) PCT No.: PCT/EP2021/051900
§ 371 (c)(1),
(2) Date: Mar. 3, 2022

(87) PCT Pub. No.: WO2021/156123
PCT Pub. Date: Aug. 12, 2021

(65) Prior Publication Data
US 2022/0401046 A1 Dec. 22, 2022

(30) Foreign Application Priority Data
Feb. 3, 2020 (EP) .................................... 20155170

(51) Int. Cl.
*A61B 6/00* (2006.01)
*A61L 2/18* (2006.01)
(Continued)

(52) U.S. Cl.
CPC .......... *A61B 6/4423* (2013.01); *A61B 6/4283* (2013.01); *A61B 6/56* (2013.01);
(Continued)

(58) Field of Classification Search
CPC ....... A61B 6/4423; A61B 6/4283; A61B 6/56; A61L 2/18; A61L 2/26; A61L 2202/17;
(Continued)

(56) References Cited

U.S. PATENT DOCUMENTS 6,137,861 A 10/2000 Reina
8,975,868 B2 * 3/2015 Konkle ................. H02J 7/0013
320/115
(Continued)

FOREIGN PATENT DOCUMENTS

CN 207949813 U 10/2018
EP 1763120 A2 3/2007
(Continued)

OTHER PUBLICATIONS

PCT International Search Report, International application No. PCT/EP2021/051900, dated Apr. 7, 2021.

*Primary Examiner* — David P Porta
*Assistant Examiner* — Djura Malevic
(74) *Attorney, Agent, or Firm* — Larry Liberchuk (57) ABSTRACT

The invention concerns a storage device for cleaning and charging portable X-ray detectors, and an X-ray system comprising such storage device. The storage device comprises a receiving unit for receiving at least one portable X-ray detector, a cleaning unit for cleaning the portable X-ray detector when being received by the receiving unit, and a charging unit for charging the portable X-ray detector, wherein the cleaning unit is configured for mechanically and/or chemically cleaning the portable X-ray detector. Further, the invention concerns a method of cleaning and charging a portable X-ray detector in a storage device.

14 Claims, 4 Drawing Sheets

(51) Int. Cl.
  *A61L 2/26* (2006.01)
  *B08B 1/00* (2006.01)
  *B08B 3/08* (2006.01)

(52) U.S. Cl.
  CPC ...... *A61L 2/18* (2013.01); *A61L 2/26* (2013.01); *B08B 1/001* (2013.01); *B08B 3/08* (2013.01); *A61L 2202/17* (2013.01)

(58) Field of Classification Search
  CPC ........... A61L 2202/122; A61L 2202/15; A61L 2202/182; A61L 2202/24; B08B 1/001; B08B 3/08
  See application file for complete search history.

(56) References Cited

U.S. PATENT DOCUMENTS

| | | | | |
|---|---|---|---|---|
| 9,839,406 | B2 * | 12/2017 | Urbon | A61B 6/4283 |
| 10,188,359 | B2 * | 1/2019 | Kim | A61L 2/10 |
| 10,405,818 | B2 | 9/2019 | Langley | |
| 10,506,995 | B2 | 12/2019 | Ninomiya | |
| 10,763,527 | B2 | 9/2020 | Ono | |
| 10,856,821 | B2 * | 12/2020 | Onobori | A61B 6/44 |
| 2006/0070384 | A1 * | 4/2006 | Ertel | G01T 1/2928 |
| | | | | 62/3.6 |
| 2010/0111395 | A1 | 5/2010 | Tamakoshi | |
| 2011/0254563 | A1 * | 10/2011 | Liu | G01R 31/69 |
| | | | | 324/705 |
| 2013/0134930 | A1 * | 5/2013 | Konkle | H02J 7/0013 |
| | | | | 320/108 |
| 2016/0317116 | A1 * | 11/2016 | Urbon | A61B 6/56 |
| 2017/0086760 | A1 * | 3/2017 | Kim | A61L 2/10 |
| 2018/0059258 | A1 | 3/2018 | MacLaughlin | |
| 2018/0116615 | A1 * | 5/2018 | Onobori | A61B 6/42 |
| 2018/0146935 | A1 * | 5/2018 | Song | G06T 5/003 |
| 2019/0049396 | A1 | 2/2019 | Murano | |
| 2021/0088513 | A1 | 3/2021 | Antognozzi | |
| 2021/0345984 | A1 * | 11/2021 | Wiese | A61B 6/54 |

FOREIGN PATENT DOCUMENTS

| | | | | |
|---|---|---|---|---|
| EP | 1763120 | A3 | 4/2013 | |
| EP | 2878264 | A1 | 6/2015 | |
| EP | 3120775 | A1 | 1/2017 | |
| JP | 2012123297 | A | 6/2012 | |
| JP | 2019130153 | A | 8/2019 | |
| KR | 20150046696 | A | 4/2015 | |
| WO | WO2013046915 | A1 | 4/2013 | |
| WO | WO-2017022153 | A1 * | 2/2017 | A61B 6/00 |
| WO | WO2017189611 | A1 | 11/2017 | |

\* cited by examiner

CLEANING AND CHARGING PORTABLE X-RAY DETECTORS

FIELD OF THE INVENTION

The invention relates to the field of storage device for portable X-ray detectors, and more specifically to a storage device for cleaning and charging portable X-ray detectors, to an X-ray system and to a method of cleaning and charging portable X-ray detectors.

BACKGROUND OF THE INVENTION

Portable X-ray detectors are used to acquire an X-ray image of a patient, wherein in the majority of the cases the patient is in direct contact with the X-ray detector. Therefore, portable X-ray detectors are frequently used components in diagnostic imaging with intensive contact to patients in a highly contaminated environment. Therefore, the X-ray detector, in particular the surface(s) of the detector, needs regular cleaning and disinfection after each examination of a patient. The medical personnel do the cleaning and disinfection of the detector. This cleaning and/or disinfection procedure is time consuming and a precise, perfect decontamination cannot be guaranteed. Further, depending on the used X-ray detector there exist various recommendations for the cleaning and disinfection procedure, which require different handling of the X-ray detectors by the medical personnel. Due to the high patient throughput, there exists a risk of residual contamination because the manually cleaning and/or disinfection may not be done properly. One procedure for cleaning X-ray detectors may be the wipe cleaning which is performed manually by the medical personnel. During wipe cleaning a cleaning agent may be used and it is important to apply the correct amount of the cleaning agent to ensure a properly cleaning of the complete surface of the X-ray detector. Due to the used wipes, a much waste is be created for cleaning just one single X-ray detector.

Further, after the cleaning and/or disinfection the X-ray detector is stored on a table or in storage slots, which are mounted on an X-ray machine. Other storage slots may be mounted on a wall next to the X-ray machine, wherein these storage slots may provide a charging of the detectors but no cleaning.

WO 2013/046915A1 discloses a storage device for cleaning and charging portable X-ray detectors.

SUMMARY OF THE INVENTION

Therefore, there exists a need for a device which is able to store the X-ray detectors and to perform the cleaning and/or disinfection for the medical personnel and which eases the process of cleaning for different types of X-ray detectors, in particular of portable X-ray detectors.

The object of the present invention is solved with the subject matter of the independent claims, wherein further embodiments are incorporated in the dependent claims.

An object of the invention is to provide a storage device for X-ray detectors, which eases and automatizes the cleaning and/or disinfection of X-ray detectors for the medical personnel, i.e. the person using the X-ray detectors for medical imaging.

According to a first aspect of the invention, a storage device for cleaning and charging portable X-ray detectors comprises a receiving unit for receiving at least one portable X-ray detector, a cleaning unit for cleaning the portable X-ray detector when being received by the receiving unit. Further, the storage device comprises a charging unit for charging the portable X-ray detector, wherein the cleaning unit is configured for mechanically and/or chemically cleaning the portable X-ray detector. The cleaning unit comprises a mechanical cleaning element configured for applying a mechanical force onto at least one surface of the received portable X-ray detector for cleaning said at least one surface of the received portable X-ray detector.

In the context of the present invention, the term "storage device" shall be understood to describe a device, which is able to hold at least one X-ray detector and/or a plurality of X-ray detectors, wherein the storage device comprises different units for receiving, cleaning and/or charging the X-ray detector(s). On the other hand, the storage device may be structurally configured in such a manner that the receiving, cleaning and/or charging may be done by at least one unit, i.e. the different processes are carried out in the same unit, wherein the receiving unit, the cleaning unit, and the charging unit may be sub portions of one single unit. For example, the storage device firstly receives the X-ray detector, secondly cleans and/or disinfects the X-ray detector and thirdly charges the X-ray detector, wherein the receiving, cleaning, and charging is done in one and the same spatial unit.

In the context of the present invention the term "cleaning" shall be understood to describe a process, which is able to perform a cleaning of the X-ray detector, wherein the cleaning comprises the removing of liquid or solid contaminations on at least one surface of the X-ray detector. For example, the removing of body liquids of a patient can be carried out with the device of the present invention. Moreover, the cleaning may simultaneously comprise a disinfection of at least one surface of the, and/or the whole, X-ray detector. For instance, the disinfection may comprise, contrary to a simple cleaning, a treatment under a certain time, which means a certain residence time of a disinfecting agent such that determined bacteria and viruses are devitalized. Therefore, the storage device automatically performs the cleaning (and disinfection) and/or charging of the X-ray detectors, such that the workflow for the medical personal is simplified and the cleaning in manually manner can be omitted. The X-ray detector will be inserted into the storage device after being used for taking a medical image of a patient. After the cleaning of the X-ray detector the detector is stored in the storage device until the cleaned (and charged) X-ray detector is used for taking another or a new medical image.

By providing an automated receiving and cleaning for portable X-ray detectors the cleaning may be standardized, which allows a more sufficient cleaning and/or disinfection, which further relates to a lower risk of disease transmission. Hence, the medical personnel and person, who is using portable X-ray detectors, have less contact with contaminated detectors.

According to an exemplary embodiment of the invention, the cleaning unit is configured for applying a fluidic chemical substance to the received portable X-ray detector.

In the context of the present invention, the term "fluidic" shall be understood to describe liquid and gaseous substances, which substances are able to clean and/or disinfect the X-ray detector. The applied fluidic chemical substances may be standard cleaning and/or disinfecting agents used for the respective X-ray detector according to a recommendation of a supplier of the X-ray detector. The storage device may be able to apply the specific amount of the chemical substances necessary for a sufficient cleaning and/or disinfection of the surface of the X-ray detector. Hence, the storage device guarantees a sufficient cleaning and/or disinfection of the X-ray detectors such that no further contamination exist in the further use.

In particular, all surfaces of the X-ray detector are mechanically cleaned by the mechanical cleaning element, wherein for all surfaces one and the same mechanical cleaning element is used. On the other hand, the cleaning unit may comprise a plurality of mechanical cleaning elements, such that each surface of the X-ray detector may be cleaned using a respective mechanical cleaning element. If more than one mechanical cleaning element is comprised, the mechanical cleaning elements may perform the cleaning for each surface sequentially, i.e. one after another, or each surface may be cleaned simultaneously by each mechanical cleaning element. Further, other combinations are possible, for example when four mechanical cleaning elements are used for four surfaces, two mechanical cleaning elements may clean two different surfaces simultaneously and the other two mechanical cleaning elements may clean the other two surfaces after the cleaning of the first two surfaces. The mechanical cleaning element may be structurally configured as a roll, which may be able to roll over at least one surface of the X-ray detector. For example, the roll comprises brushes, which mechanically remove the body liquids on the X-ray detector. The mechanical cleaning element may also be structurally configured as an automatically wiping towel, wiping over at least one surface of the X-ray detector. Further, the mechanical cleaning element may be configured as a pulling blade and/or a scraper, pulling/scraping over a surface of the X-ray detector such that the dirt may be scraped off the surface of the X-ray detector.

According to an exemplary embodiment of the invention, the cleaning unit comprises a fluidic system for applying agents for cleaning and/or disinfecting the received portable X-ray detector.

For example, the fluidic system is configured for applying a specific amount of the agents for cleaning and/or disinfecting, such that a manually measuring of the specific amount is obsolete for the medical personnel. The fluidic system further comprises an inlet for receiving the (fresh unused) agent and an outlet for releasing the used agent, wherein the used agent is for example the contaminated agent after cleaning and/or disinfection of the X-ray detector. In particular, the fluidic system comprises the inlet for receiving the agent for cleaning, wherein the agent is inserted by user into a chamber of the fluidic system. The chamber of the fluidic system may be used to store the agent until it is delivered (automatically) for cleaning and disinfecting. Further, the chamber of the fluidic system may be configured for receiving packaged agents, for example packaged cleaning fluids (packaged in a bottle). Further, the fluidic system may comprise a further inlet inside the storage device, which further inlet may be configured for receiving the used agent, which means the agent has been used for cleaning such that the agent now comprises contaminated material. Furthermore, the fluidic system may comprise a further outlet, wherein the further outlet is configured for releasing the fresh agent to the X-ray detector. The further outlet may be a nozzle injecting the agent onto the x-ray detector. For example, a plurality of nozzles may be used injecting the fresh agent onto all surfaces of the X-ray detector.

Summarizing the fluidic system may comprise a chamber for receiving the fresh cleaning agent (a liquid agent, or a gas stored inside the storage device) and a further chamber for receiving the used cleaning agent; it may further comprise an inlet for receiving the cleaning agent, a further inlet for receiving the used agent; further it may comprise an outlet for applying the fresh agent to the X-ray detector to be cleaned and a further outlet for dispensing the used agent outside of the cleaning unit and/or outside of the storage device. A tubing system, stiff and/or flexible, may be arranged for connecting the inlet with the further outlet and the further inlet with the outlet, or any combinations thereof.

Moreover, the fluidic system may be used to apply in particular liquid substances and/or gaseous substances onto the X-ray detector for cleaning and/or for disinfection.

When using fluidic agents for cleaning and/or disinfecting the X-ray detector the cleaning unit may be structurally configured for hermetically sealing, for example by syringes, the X-ray detector from its surrounding in such a manner that the cleaning agents will not be dispensed to the outside of the cleaning unit. If the cleaning unit is sealed the cleaning unit may be structurally configured that the X-ray detector may be flooded inside of the cleaning unit, such that the X-ray detector may be completely surrounded by the fluidic chemical substance. For instance, a gaseous substance may be flooded inside of the cleaning unit, surrounding the whole X-ray detector for cleaning and disinfecting.

According to an exemplary embodiment of the invention, the charging unit is configured for charging the portable X-ray detector before and/or during and/or after the cleaning carried out by the cleaning unit.

In particular, the charging of the X-ray detector may starts before the cleaning has started and will be carried on during the cleaning and if the X-ray detector is not fully charged after the cleaning has been finished the charging may hold on after the cleaning. On the other hand, the charging may start during the cleaning and may last the whole cleaning process and beyond. Further, the charging of the X-ray detector will start after the cleaning of the X-ray detector. For example, using a supercapacitor, which is integrated into an X-ray detector, may enable a charging in a contactless manner and in a very high repetition rate. The supercapacitor is a high-capacity capacitor with a capacitance value much higher than other capacitors, but with low voltage limits and which stores 10 to 100 times more energy per unit volume or mass than electrolyte capacitors, such that it can accept and deliver charge much faster than batteries and tolerates many more charge and discharge cycles than rechargeable batteries. Hence, using contactless charging enables the storage device for simultaneously cleaning and charging the X-ray detector.

Further, the charging may be performed by an electrical interface wherein the X-ray detector may be plugged on a charging mechanism inside the charging unit for charging. When using liquid chemical substances, the connection between the X-ray detector and the charging mechanism may be sealed for preventing liquid income to the charging mechanism. For receiving, cleaning, and/or charging the X-ray detector, the storage device may be connected to a power supply system by cable. If the storage device is used in connection with an X-ray system, the storage device may be connected to the power supply system by the X-ray system. Furthermore, the storage device may be autonomous, independent, of a power supply wherein the storage device may be battery powered.

According to an exemplary embodiment of the invention, the mechanically and/or chemically cleaning is conducted inside the storage device in such a manner that the cleaning, in particular a start of the cleaning, is performed without interaction of a user. Hence, no explicit action for starting the cleaning process is required by a user, except the insertion of the X-ray detector into the storage device. The cleaning may start immediately when received in the storage device or in particular when received in the cleaning unit. The user does not need to activate a start button for starting the cleaning.

According to an exemplary embodiment of the invention, the storage device further comprises a status indicator for displaying to a user of the storage device whether the storage device is currently cleaning and/or charging. Further, the status indicator displays whether the storage device is currently disinfecting and/or mechanically cleaning and/or chemically cleaning and/or whether the X-ray detector needs maintenance in form of a software update, and/or whether the cleaning agent needs to be refilled. Any combination of the previous mentioned features may be possible to be displayed by the status indicator. In the context of the present invention the term "currently" shall be understood to describe, that the storage device at the present time indicates to the user the actually status of the storage device or the status of the processes carried out by the storage device. For instance, the storage device may always indicate its status when plugged into the power supply system.

According to an exemplary embodiment of the invention, the status indicator is embodied as one or more LEDs, a display, a sound emitter, or any combination thereof. For example, when using a display all status referring for example to a maintenance, filling level of cleaning agent, charging status of X-ray detector, cleaning (disinfecting) status of the X-ray detector may be simultaneously displayed.

According to an exemplary embodiment of the invention, the storage device further comprises a release mechanism configured for releasing the received portable X-ray detector upon an activation of the release mechanism by a user. In particular, the release mechanism is configured for releasing the X-ray detector out of the storage device for further use. For instance, the release mechanism may release the X-ray detector directly to an X-ray system such that the X-ray detector may be inserted into the X-ray system for being used for medical imaging. The release mechanism may be configured to just release the X-ray detector when a predetermined user activates the release mechanism.

According to an exemplary embodiment of the invention, the release mechanism comprises a touchscreen and/or a fingerprint detector. In particular, a fingerprint detector may be used for securing the X-ray detector of unwanted use by other persons and for securing the data of the patient. In other words, the X-ray detector is locked inside the storage device unless a user activates the release mechanism.

According to an exemplary embodiment of the invention, the storage device may be structurally configured for providing a maintenance for the received portable X-ray detector. For example, the storage device comprises a maintenance unit configured for maintain the received portable X-ray detector. On the other hand, an existing unit, for example the charging unit of the storage device, may be configured to provide maintenance for the received portable X-ray detector. In the context of the present invention the term "maintenance" shall be understood to describe a service for the received portable X-ray detector, like actualizing a software of the X-ray detector, or configuring the portable X-ray detector (outside of the X-ray system), reading out the image of the patient of the X-ray detector, and enable the user to do diagnosis on the basis of the image on the received portable X-ray detector. For example, a connection to an external device (like a Computer) may enable the user to read and write data in the storage device and/or in the portable X-ray detector. LAN and/or WLAN may provide the connection to the external device. Therefore, the storage device enables maintenances and diagnosis for the user, even during cleaning, which eases and fastens the service process for a reuse of a portable X-ray detector. Further, the contact to contaminated X-ray detectors is reduced as the maintenance and diagnosis can be carried out even when the portable X-ray detector is received (and cleaned) in the storage device.

According to an exemplary embodiment of the invention, the storage device further comprises one or more portable X-ray detectors received in the receiving unit, and wherein the one or more portable X-ray detectors are selected from a CR detector, and a DR detector. The storage device may be configured for storing (and receiving, cleaning, disinfecting, and/or charging) a plurality of CR detectors or a plurality of DR detectors. On the other hand, the storage device may be used for CR detectors and DR detectors simultaneously. A CR detector may be a cassette with photostimulable phosphors to be read out by a reader. A CR detector may be inserted into the reader after every image created. In particular, for a CR detector the storage device may be able to readout the image data when received in the receiving unit or in the charging unit. The storage device may receive more than one CR detector and may be able to read out more than one CR detector at the same time. In mechanically aspects the CR and DR detectors may be compatible with each other, such that none (or only minor) constructive adaption of the storage device may be necessary when the storage device is used for both kinds of X-ray detectors. For instance, the charging unit may be adapted for charging the DR detectors and for read out the CR detectors, such that the same charging unit may be used for both kinds of X-ray detectors. According to this embodiment, only an adaption of the charging unit may be necessary for providing charging and reading but no adaption of the receiving unit and the cleaning unit is necessary.

According to an exemplary embodiment of the invention, the charging unit is configured for charging batteries, in particular external batteries, of X-ray detectors. The charging unit may be able to charge at least one external battery or a plurality of external batteries of X-ray detectors. For example instead of the X-ray detector the external battery may be inserted into the charging unit. The charging of external batteries may be applicable for each embodiment of the charging unit.

According to an exemplary embodiment of the invention, the storage device is configured for cleaning and/or charging a plurality of portable and received X-ray detectors sequentially one after another or simultaneously in the cleaning unit of the storage device. In particular, the plurality X-ray detectors are automatically cleaned sequentially and/or simultaneously. According to this embodiment, the cleaning unit and the charging unit may form one single unit, wherein the cleaning and the charging can be carried out simultaneously. For example for a plurality of X-ray detectors, the storage device comprises a plurality of combined cleaning-charging units. For instance, the storage device may be configured for receiving, cleaning, and charging four X-ray detectors, each X-ray detector is received by a separate receiving unit and processed to a respective cleaning-charging unit, such that the storage device comprises four receiving units and four cleaning-charging units. On the other hand, the storage device may comprise one receiving unit and one cleaning unit but four charging units, wherein the four X-ray detectors may be processed through the receiving and cleaning unit separately but may be charged simultaneously in a respective charging unit. Other combinations of the amount of receiving unit, charging unit, and cleaning unit may be possible.

According to an exemplary embodiment of the invention, the receiving unit is configured for receiving portable X-ray detectors having a size in a range of 18 cm×24 cm to 35 cm×43 cm, preferably 43 cm×43 cm. In particular, the size of the receiving unit is configured to receive an X-ray detector that is 15×30 cm, 18×24 cm, 24×30 cm, 35×35 cm, and 35×43 cm. Further, the storage device may be applicable for other X-ray detector sizes used for example in dental medical X-ray applications.

According to a second aspect of the invention, an X-ray system comprises an apparatus for generating X-ray images of a patient, a portable X-ray detector, and a storage device according to any of the preceding embodiments, in which the portable X-ray detector of the X-ray system can be stored. In particular, the X-ray system may comprise a plurality of X-ray detectors which plurality may be stored and cleaned inside of the storage device.

According to an exemplary embodiment of the invention, the storage device is stationary and/or removably coupled to the X-ray system. In other words, the storage device may be a stand-alone device or attached to an X-ray system. According to this embodiment for each respective X-ray system one storage device may be provided. On the other side, a plurality of X-ray systems may use one single storage device, for example when the storage device is used for a plurality of X-ray detectors, such that they share one mobile storage device.

According to a third aspect of the invention, a method of cleaning and charging a portable X-ray detector in a storage device comprises the steps of receiving at least one portable X-ray detector in a receiving unit of the storage device (S1), mechanically and/or chemically cleaning the portable X-ray detector by a cleaning unit of the storage device while being received by the receiving unit (S2), applying a mechanical force by a mechanical cleaning element of the cleaning unit onto at least one surface of the received portable X-ray detector, and charging the portable X-ray detector by a charging unit of the storage device (S3). The method may comprise cleaning and charging a plurality of portable X-ray detectors. The steps of receiving, cleaning and charging may be performed sequentially one after another or may be at least partially performed simultaneously. In particular, the cleaning and charging step may be performed at the same time and the cleaning may directly start when the X-ray detector is inserted into the receiving unit, wherein the cleaning may start immediately when a first part is received in the storage device and another part is still outside of the receiving unit and still is inserted into the receiving unit. Further, the cleaning and charging of a plurality of X-ray detectors may be performed sequentially one after another or may be at least partially performed simultaneously.

According to an exemplary embodiment of the invention, the method further comprises the step of applying a fluidic chemical substance to the received portable X-ray detector by the cleaning unit. In particular, the applying of the fluidic chemical substance may comprise determining an amount necessary for sufficiently cleaning (and/or disinfecting) the X-ray detector, wherein the amount may be determined in dependence of the size of the X-ray detector and/or in dependence of a recommendation of a supplier of the X-ray detector. After determining the amount of the chemical substance, it is applied on the X-ray detector for cleaning and/or disinfecting.

According to the invention, the method comprises the step of applying a mechanical force by a mechanical cleaning element of the cleaning unit onto at least one surface of the received portable X-ray detector. Further, the step may comprise applying the mechanical force by the mechanical cleaning element of the cleaning unit onto all surfaces of the received portable X-ray detector. Furthermore, the step may comprise applying a mechanical force by a plurality of mechanical cleaning elements to at least one surface (and/or to a plurality of surfaces) of the received portable X-ray detector.

According to an exemplary embodiment of the invention, the method further comprises charging the portable X-ray detector before and/or during and/or after the cleaning carried out by the cleaning unit.

BRIEF DESCRIPTION OF THE DRAWINGS

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

DETAILED DESCRIPTION OF EMBODIMENTS

Figure 1:
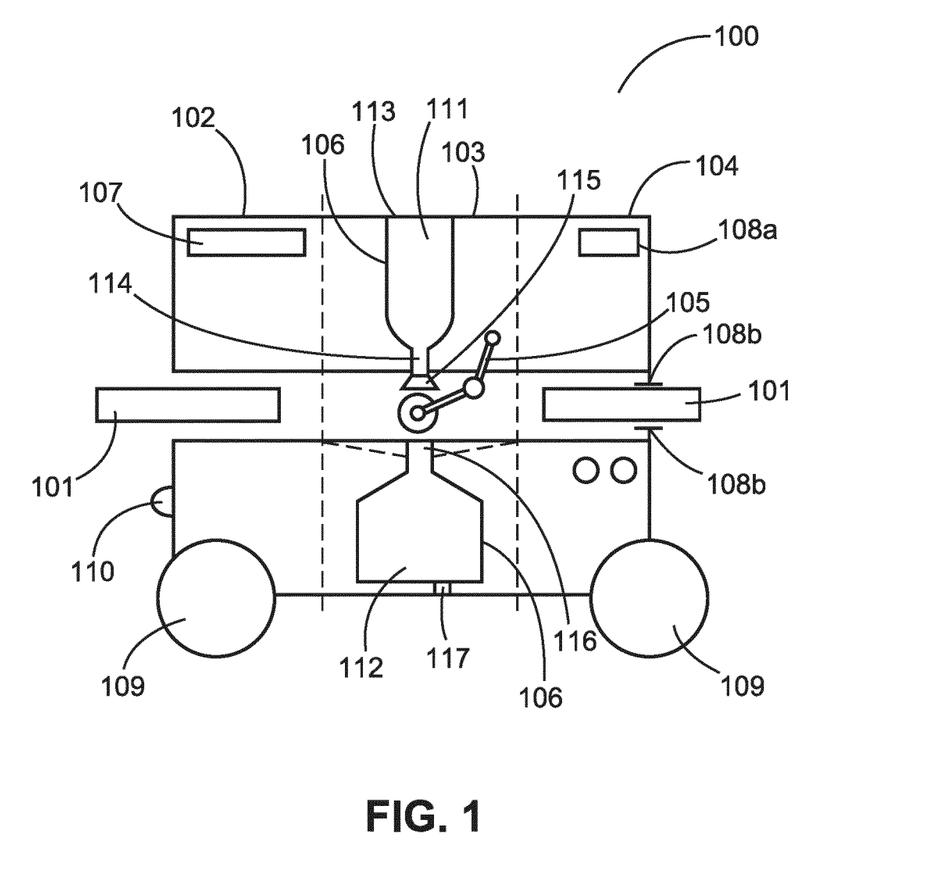
FIG. 1 illustrates a storage device for portable X-ray detectors according to an exemplary embodiment of the invention.

FIG. 1 illustrates a side view of a storage device (100) for cleaning and charging portable X-ray detectors (101). The storage device (100) comprises a receiving unit (102) for receiving at least one portable X-ray detector (101), a cleaning unit (103) for cleaning the portable X-ray detector (101) when being received by the receiving unit (102), a charging unit (104) for charging the portable X-ray detector (101), and wherein the cleaning unit (103) is configured for mechanically and/or chemically cleaning the portable X-ray detector (101). The mechanically and/or chemically cleaning is conducted inside the storage device (100) in such a manner that the cleaning, in particular a start of the cleaning, is performed without interaction of a user. The storage device (100) is configured as a mobile storage device, for example the storage device (100) comprises wheels (109) for moving the storage device (100) to a desired position. Further, the storage device (100) may be coupleable to an X-ray system, this connection is indicated by the connector (110), wherein the connector is formed in such a manner that it fits to a respective X-ray system or to a plurality of X-ray systems. The connector (110) may be any kind of coupling used for coupling devices to X-ray systems.

The cleaning unit (103) is configured for applying a fluidic chemical substance (not illustrated) to the received portable X-ray detector (101). The cleaning unit (103) comprises a fluidic system (106) for applying agents for cleaning and/or disinfecting the received portable X-ray detector (101). As illustrated in FIG. 1 the fluidic system (106) comprises an inlet (113) for receiving the fresh cleaning substance (chemical substance, liquid or gaseous form), wherein the cleaning substance may be stored in the chamber 111. Further, the fluidic system (106) comprises a further outlet (114) arranged after the chamber (111), wherein the further outlet (114) applies the fresh cleaning substance to the received X-ray detector (101) for example by a nozzle (115). It may also be possible to use a plurality of nozzles (115) for applying the cleaning substance to the X-ray detector. In this embodiment, the nozzle is arranged above the received X-ray detector. It may also be possible to arrange the nozzle (115) at different positions or to arrange a plurality of nozzles (115) above, below, and on the sides of the received X-ray detector. The fluidic system (106) further comprises a further inlet (116) below the received X-ray detector, wherein the further inlet (116) is configured for receiving the used cleaning substance. The used cleaning substance may be stored in a further chamber (112) before it is released out of the storage device (100) through an outlet (117). The applying of the fresh cleaning substance may be performed automatically by the storage device. For example, the receiving unit (102) comprises a sensor for detecting which kind and/or which size of detector (101) is received. Depending on the sensed X-ray detector (101), the respective cleaning procedure is chosen, i.e. chemically or mechanically. Further, if the chemically cleaning procedure is selected the storage device (100), in particular the cleaning unit (103), determines the agent to be used for the respective X-ray detector (101) and the amount of the agent to be applied on the X-ray detector (101) by the nozzles (115).

The cleaning unit (103) further comprises a mechanical cleaning element (105) configured for applying a mechanical force onto at least one surface of the received portable X-ray detector (101) for cleaning said at least one surface of the received portable X-ray detector (101). The mechanical cleaning element (105) may comprise different components like arms and joints being connected to each other, such that the mechanical element (105) may be freely movable inside the cleaning unit (103) and on at least one surface of the received X-ray detector (101). Further, the mechanical cleaning element (105) comprises a brush at it end for mechanically cleaning the X-ray detector (101). As can be seen in FIG. 1, the mechanical cleaning element (105) is arranged above the X-ray detector to be cleaned. It may also be possible to arrange a plurality of mechanical cleaning elements (105) inside the cleaning unit (103), for example they may be arranged above and below the received X-ray detector (101).

The charging unit (104) is configured for charging the portable X-ray detector (101) before and/or during and/or after the cleaning carried out by the cleaning unit (103). For example. The charging unit (104) may comprise an inductive charging element, which may be arranged in the charging unit (104) and may further be at least partly arranged in the cleaning unit (103), such that the charging may be started during the cleaning of the X-ray detector (101).

The storage device further comprises a status indicator (107) for displaying to a user of the storage device (100) whether the storage device (100) is currently cleaning and/or charging. The status indicator (107) is embodied as one or more LEDs, a display, a sound emitter, or any combination thereof. The status indicator (107) in this embodiment is arranged on the outside of the storage device (100), in particular at the receiving unit (107). The status indicator (107) may be arrangeable at any position on the storage device (100). The storage device further comprises a release mechanism (108) configured for releasing the received portable X-ray detector (101) upon an activation of the release mechanism (108) by a user, wherein the release mechanism (108) comprises a touchscreen (108a) and/or a fingerprint detector. In FIG. 1, the release mechanism (108) comprises a touchscreen (108a) and a holder (108b) holding the X-ray detector (101) at least two sides. The holder (108b) may be constructed in form of a clamp (108b) which will only open after the activation of the touchscreen (108a) by fingerprint. The construction of the release mechanism may not be limited to a holder, clamp, other holding and releasing mechanism may also be possible. The touchscreen (108a) and the finger print detector of the release mechanism (108) may be integrated in the status indicator (107), such that for example one display may be used for the status indicator (107) and the release mechanism (108).

As can be seen in FIG. 1, the storage device (100) comprises one or more portable X-ray detectors (101), in FIG. 1 two X-ray detectors (101), one received in the receiving unit (102) and another one arranged in the charging unit (104), wherein the one or more portable X-ray detectors (101) are selected from a CR detector, and a DR detector. As illustrated in FIG. 1, the storage device (100) is configured for cleaning and/or charging a plurality of portable and received X-ray detectors (101) sequentially one after another in the cleaning unit (103) of the storage device (100). The X-ray detectors (101) are received at one side of the storage device (100) and transported, for instance in a production line or flat conveyor manner, to the other side of the storage device (100), wherein during the transportation to the other side the X-ray detector (101) is cleaned an charged. An illustration of the simultaneously cleaning and/or charging a plurality of portable and received X-ray detectors (101) in the cleaning unit (103) of the storage device (100) is shown in FIG. 2.

Figure 2:
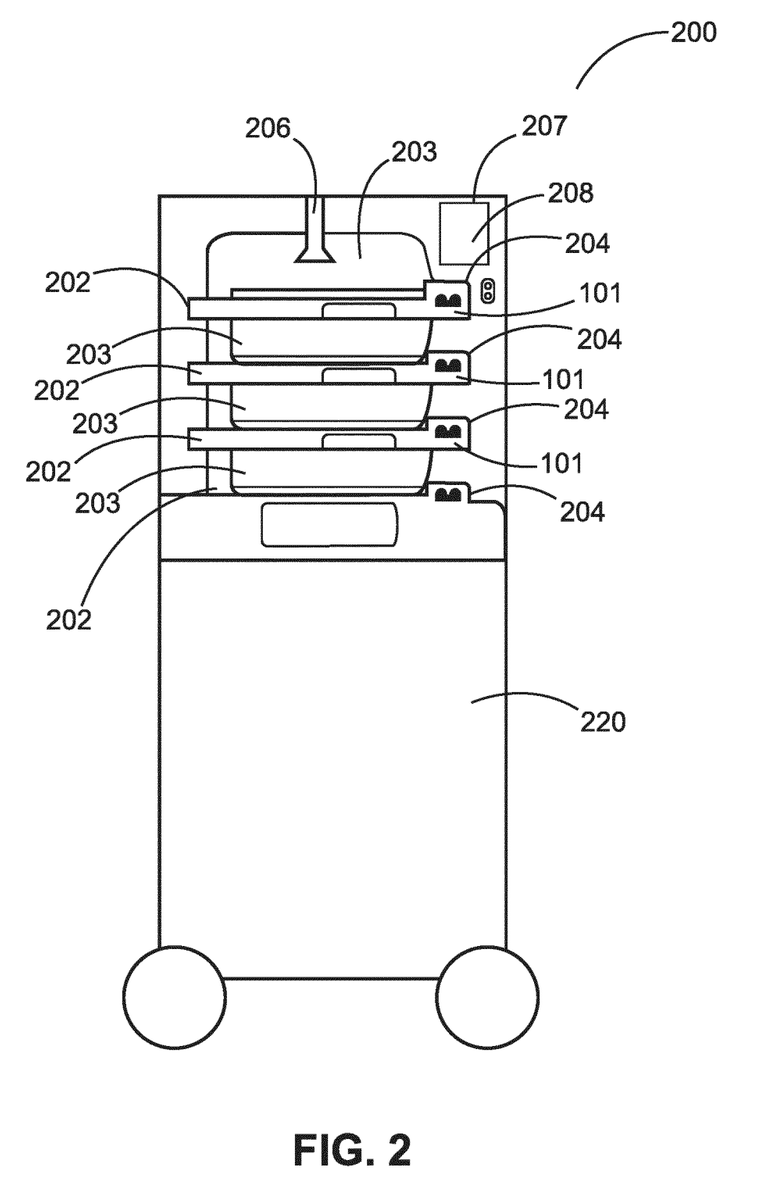
FIG. 2 illustrates a further storage device for portable X-ray detectors according to an exemplary embodiment of the invention.

FIG. 2 illustrates an embodiment of the storage device (200) according to the present invention, wherein the storage device (200) is configured to receive a plurality of X-ray detectors (101). In particular, the storage device (200) in FIG. 2 can receive four X-ray detectors (101). FIG. 2 illustrates a front view of the storage device (200). The storage device (200) in this embodiment comprises four receiving units (202), four cleaning units (203) and four charging units (204) for each respective X-ray detector (101). On the other hand, the cleaning units (203) may be configured as one cleaning unit (204), wherein the four X-ray detectors are cleaned simultaneously by one cleaning unit (204), in particular by the fluidic system (206) of the cleaning unit (204), wherein the inlet of the fluidic system (206) is arranged above all X-ray detectors, which are arranged above each other, such that a cleaning substance applied by the inlet of the fluidic system (206) will reach all X-ray detectors (101). The outlet of the fluidic system (206) may be arranged below all four X-ray detectors (101). Further, the cleaning units (203) comprise a mechanical cleaning element (not illustrated), wherein each cleaning unit (203) may comprise a respective mechanical cleaning element or more than one mechanical cleaning element. According to this embodiment, the X-ray detectors (101) are arranged above another and are not processed in a flat conveyor manner through the storage device (as described with FIG. 1). The X-ray detectors (101) are inserted, i.e. received at one side of the storage device (200), and will also be released after cleaning and charging on the same side of the storage device (200). The status indicator (207) may be a display or a touchscreen, wherein the release mechanism (208) (in particular the fingerprint detector) may be integrated in the status indicator (207). Further, the storage device (200) comprises a maintenance unit (220) which is configured for maintain the X-ray detectors (101). In particular, the maintenance (220) may enable a data read out of the received X-ray detectors (101) or enable a software update of the received X-ray detectors (101). The maintenance unit (220) may not be visible to a user, as it is integrated inside of the storage device (200). The storage device (200) may be closed after receiving the X-ray detectors (101) by a housing, which for example may be a door closing the front of the storage device (200). In the storage device (220) according to this embodiment, the fluidic system (206) may be also comprise all the components as described with the embodiment of FIG. 1, wherein not all components of the fluidic system (206) are illustrated in FIG. 2.

Figure 3:
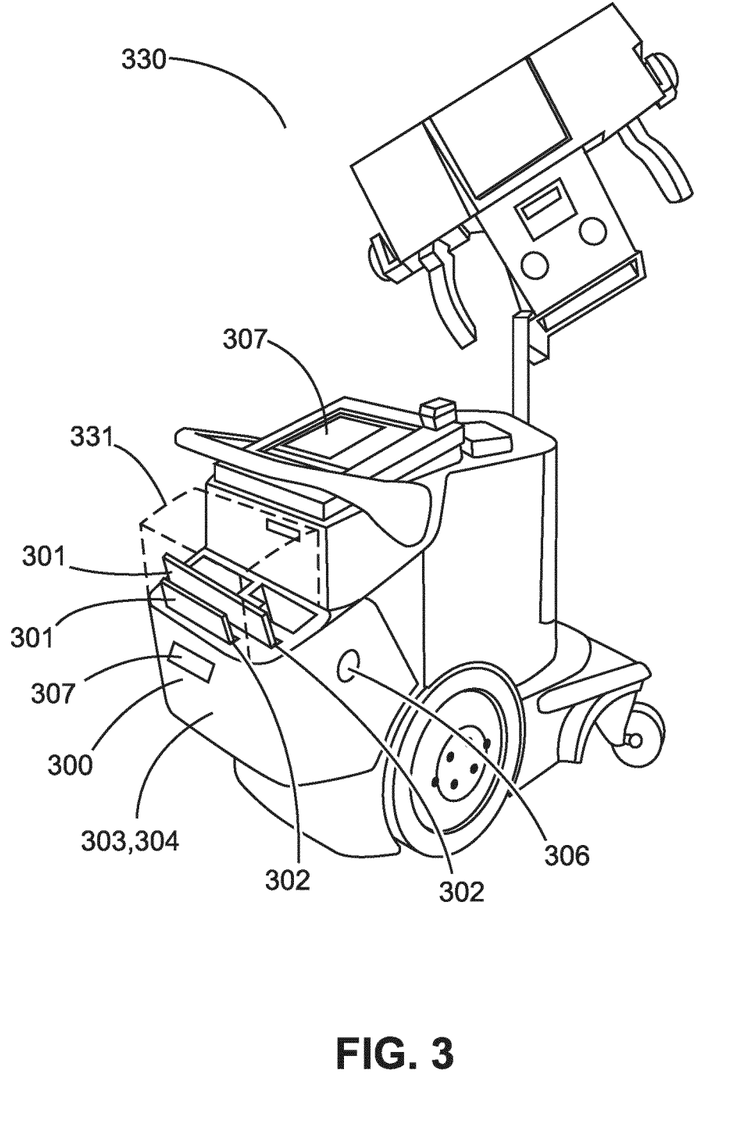
FIG. 3 illustrates an X-ray system comprising a storage device for portable X-ray detectors according to an exemplary embodiment of the invention.

FIG. 3 illustrates a X-ray system (330) comprising an apparatus for generating X-ray images of a patient, a portable X-ray detector (301), and a storage device (100), in which the portable X-ray detector (301) of the X-ray system (330) can be stored. The X-ray system (330) comprises a storage device (300) according to an embodiment of the present invention. The storage device (300) is stationary integrated on the X-ray system (330), wherein according to this embodiment the X-ray system (330) is movable. In other embodiments, the storage device (300) may be removably coupled to the X-ray system (330). The storage device (300) comprises for instance two receiving units (302), wherein each receiving unit (302) is configured for receiving portable X-ray detectors (301) having a size in a range of 18 cm×24 cm to 35 cm×43 cm, preferably 43 cm×43 cm. Further, the storage device (300) comprises two cleaning units (303) and two charging units (304). The status indicator (307) is attached to the storage device (300) on the other side the status indicator (307) may be integrated in the status indicator (307) of the X-ray system (the indicator (307) above the storage device (300)). The fluidic system (306) of the cleaning unit (303) is integrated inside of the storage device (300), only the inlet of the fluidic system (306) is visible in FIG. 3. The fluidic system (306) may comprise all elements has described with FIG. 1. The storage device (300) comprises a housing (331) attached above the receiving (302), cleaning (303), and charging unit (304). For each respective X-ray detector there exist one receiving unit (302), one cleaning unit (303) and charging unit (304).

Figure 4:
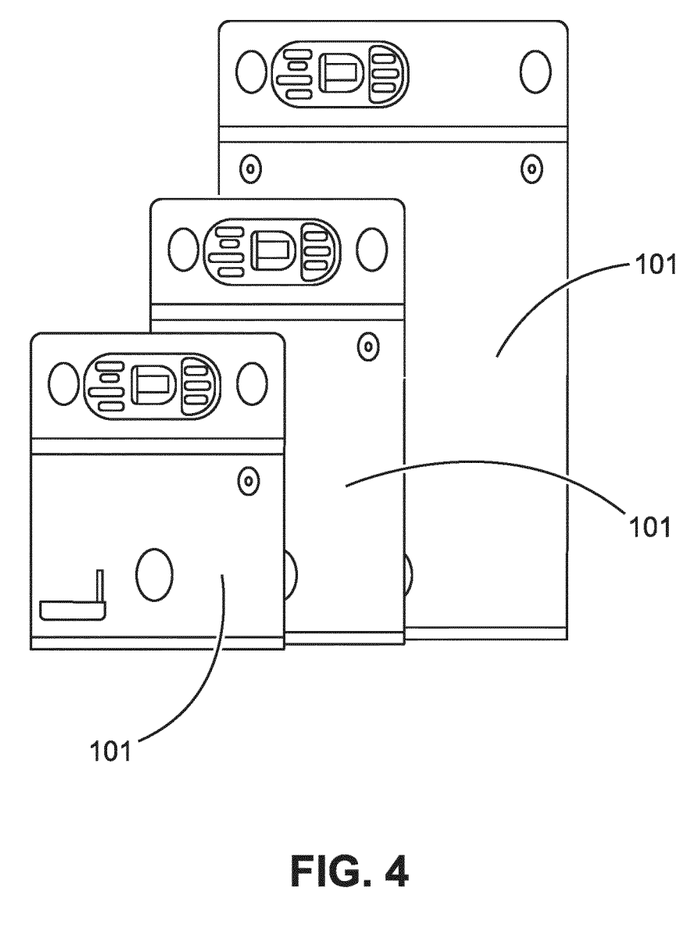
FIG. 4 illustrates portable X-ray detectors for being used in a storage device according to an exemplary embodiment of the invention.

FIG. 4 illustrates different sizes of X-ray detectors (101), wherein the storage device (100, 200, 300) is configured for receiving, cleaning, and charging these X-ray detectors (101). In particular, one and the same storage device is configured for receiving X-ray detectors (101) with different sizes or one and the same storage device is configured for receiving X-ray detectors (101) having only the same size. Further, the storage device may be configured for receiving different kinds of X-ray detectors, for example the storage device may be configured for receiving CR detectors, in particular CR cassettes, and DR detectors.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

LIST OF REFERENCE SIGNS 100, 200, 300 storage device
101, 301 X-ray detector
102, 202, 302 receiving unit
103, 203, 303 cleaning unit
104, 204, 304 charging unit
105 mechanical cleaning element
106, 206, 306 fluidic system
107, 207, 307 status indicator
108, 208 release mechanism
109 wheel
110 connector
111 chamber
112 further chamber
113 inlet
114 further outlet
115 nozzle
116 further inlet
117 outlet
220 maintenance unit
330 X-ray system
331 housing

The invention claimed is:

1. Storage device for cleaning and charging portable X-ray detectors, comprising
a receiving unit for receiving at least one portable X-ray detector,
a cleaning unit for cleaning the portable X-ray detector when being received by the receiving unit,
a charging unit for charging the portable X-ray detector, wherein the cleaning unit is configured for mechanically and/or chemically cleaning the portable X-ray detector, wherein the cleaning unit comprises a mechanical cleaning element configured for applying a mechanical force onto at least one surface of the received portable X-ray detector for cleaning said at least one surface of the received portable X-ray detector.

2. Storage device according to claim 1, wherein the cleaning unit is configured for applying a fluidic chemical substance to the received portable X-ray detector.

3. Storage device according to claim 1, wherein the cleaning unit comprises a fluidic system for applying agents for cleaning and/or disinfecting the received portable X-ray detector.

4. Storage device according to claim 1, wherein the charging unit is configured for charging the portable X-ray detector before and/or during and/or after the cleaning carried out by the cleaning unit.

5. Storage device according to claim 1, wherein the mechanically and/or chemically cleaning is conducted inside the storage device in such a manner that the cleaning is performed without interaction of a user.

6. Storage device according to claim 1, further comprising a status indicator for displaying whether the storage device is currently cleaning and/or charging.

7. Storage device according to claim 6, wherein the status indicator is embodied as one or more LEDs, a display, a sound emitter, or any combination thereof.

8. Storage device according to claim 1, further comprising a release mechanism configured for releasing the received portable X-ray detector upon an activation of the release mechanism by a user.

9. Storage device according to claim 8, wherein the release mechanism comprises a touchscreen and/or a fingerprint detector.

10. Storage device according to claim 1, further comprising one or more portable X-ray detectors received in the receiving unit, and wherein the one or more portable X-ray detectors are selected from a CR detector, and a DR detector.

11. Storage device according to claim 10, wherein the storage device is configured for cleaning and/or charging a plurality of portable and received X-ray detectors sequentially one after another or simultaneously in the cleaning unit of the storage device.

12. Storage device according to claim 1, wherein the receiving unit is configured for receiving portable X-ray detectors having a size in a range of 18 cm×24 cm to 35 cm×43 cm.

13. X-ray system, comprising:
an apparatus for generating X-ray images of a patient,
a portable X-ray detector, and
a storage device for cleaning and charging portable X-ray detectors, comprising:
a receiving unit for receiving at least one portable X-ray detector;
a cleaning unit for cleaning the portable X-ray detector when being received by the receiving unit;
a charging unit for charging the portable X-ray detector, wherein the cleaning unit is configured for mechanically and/or chemically cleaning the portable X-ray detector, wherein the cleaning unit comprises a mechanical cleaning element configured for applying a mechanical force onto at least one surface of the received portable X-ray detector for cleaning said at least one surface of the received portable X-ray detector, in which the portable X-ray detector of the X-ray system is stored.

14. Method of cleaning and charging a portable X-ray detector in a storage device, the method comprising:
receiving at least one portable X-ray detector in a receiving unit of the storage device,
mechanically and/or chemically cleaning the portable X-ray detector by a cleaning unit of the storage device while being received by the receiving unit,
applying a mechanical force by a mechanical cleaning element of the cleaning unit onto at least one surface of the received portable X-ray detector, and
charging the portable X-ray detector by a charging unit of the storage device.

* * * * *